US008005325B2

(12) United States Patent
Arkwright (10) Patent No.: US 8,005,325 B2
(45) Date of Patent: Aug. 23, 2011

(54) APPARATUS FOR SENSING A MOTION (75) Inventor: John William Arkwright, Ryde (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 12/735,045

(22) PCT Filed: Dec. 1, 2008

(86) PCT No.: PCT/AU2008/001775
§ 371 (c)(1),
(2), (4) Date: Aug. 4, 2010

(87) PCT Pub. No.: WO2009/073913
PCT Pub. Date: Jun. 18, 2009

(65) Prior Publication Data
US 2010/0296772 A1 Nov. 25, 2010

(30) Foreign Application Priority Data

Dec. 11, 2007 (AU) ................................ 2007906733

(51) Int. Cl.
*G02B 6/00* (2006.01)
*G02B 6/34* (2006.01)
(52) U.S. Cl. .......... 385/13; 385/12; 385/37; 250/227.14
(58) Field of Classification Search ............ 385/12, 385/13, 37; 250/227.14
See application file for complete search history.

(56) References Cited

U.S. PATENT DOCUMENTS

| 6,218,661 | B1 * | 4/2001 | Schroeder et al. | 250/227.14 |
| 6,774,354 | B2 * | 8/2004 | Ames | 250/227.14 |
| 6,898,339 | B2 * | 5/2005 | Shah et al. | 385/13 |
| 7,388,190 | B2 * | 6/2008 | Huang et al. | 250/227.14 |
| 2001/0019103 | A1 | 9/2001 | Sugai et al. | |
| 2006/0200049 | A1 | 9/2006 | Leo et al. | |

FOREIGN PATENT DOCUMENTS
WO    WO 2006/094353    9/2006

OTHER PUBLICATIONS

International Search Report for PCT/AU2008/001775, mailed Feb. 3, 2009.
International Preliminary Report on Patentability for PCT/AU2008/001775, dated Apr. 12, 2010.

* cited by examiner

*Primary Examiner* — Daniel Petkovsek
(74) *Attorney, Agent, or Firm* — Nixon & Vanderhye P.C.

(57) ABSTRACT

The present disclosure provides an apparatus for sensing a motion. The apparatus comprises an optical fibre portion comprising a Bragg grating and an element for reducing an impact of an external force that is transversal to the Bragg grating. Further, the apparatus comprises a contact region arranged so that movement of a further region, that is in direct or indirect contact with the contact region and moves in a direction along a portion of the apparatus, causes movement of the optical fibre portion at the contact region. The apparatus also comprises a holder arranged for reducing movement of the optical fibre portion at a holding region when the optical fibre portion is moved at the contact surface. The apparatus is arranged so that movement of the contact region relative to the holding region causes a change in strain of the Bragg grating.

19 Claims, 6 Drawing Sheets

APPARATUS FOR SENSING A MOTION

This application is the U.S. national phase of International Application No. PCT/AU2008/001775 filed 1 Dec. 2008 which designated the U.S. and claims priority to AU Patent Application No. 2007906733 filed 11 Dec. 2007, the entire contents of each of which are hereby incorporated by reference.

FIELD OF THE INVENTION

The present invention broadly relates to an apparatus for sensing a motion.

BACKGROUND OF THE INVENTION

The human body has many regions in which pressure differences cause matter to move. For example, the human heart pumps blood through the body. Muscles around the alimentary canal apply a pressure to the canal, which moves food from the mouth into the stomach.

Monitoring pressures and motion in the human body can provide important information about the function of the human body and can be used to detect disorders and diseases or can be used to control a recovery from a disease.

Optical devices for monitoring pressures within a body lumen are now being developed. Such optical devices are typically very narrow and consequently do not cause too much discomfort to a patient. The optical devices may comprise an optical fibre Bragg grating, which has an optical response that depends on a strain of the Bragg grating. The strain of the Bragg grating is applied by a "squeezing" force in the vicinity of the Bragg grating and the resultant increase in strain shifts a wavelength of an optical response to a longer wavelengths range.

However, important information directly characterising a longitudinal motion, such as a motion of bolus along the oesophagus effected by muscles of the oesophagus, or longitudinal motion of the oesophageal wall itself, cannot be provided in a convenient manner using known devices.

SUMMARY OF THE INVENTION

The present invention provides in a first aspect an apparatus for sensing a motion, the apparatus comprising:
  a length of an optical fibre comprising a Bragg grating;
  an element for reducing an impact of an external force that is transversal to the Bragg grating;
  a contact region coupled to a first portion of the length of the optical fibre and arranged so that movement of a further region, that is in direct or indirect contact with the contact region and moves relative to the apparatus in a direction along a portion of the apparatus, causes movement of the length of the optical fibre at the first optical fibre portion; and
  a holder arranged for reducing movement of the length of the optical fibre at a second portion of the length of the optical fibre when the optical fibre portion is moved at the first optical fibre portion;
  wherein the apparatus is arranged so that movement of the contact region relative to the holder causes a change in strain of the Bragg grating.

It has been observed that muscles along the oesophagus contract and expand in a longitudinal direction such that, when combined with a radial contraction, a movement is caused that moves a bolus along the oesophagus. Known devices for measuring a transverse pressure in the oesophagus cannot detect a movement in a longitudinal caused by a contraction or expansion of the oesophagus.

A medium that in use surrounds the apparatus according to the present invention may frictionally engage with side-portions of the apparatus. A local longitudinal movement of an external medium that is in frictional contact with the contact region (ether directly or indirectly) effects a longitudinal movement of that portion relative to the holding portion and results in a change in strain of the Bragg grating. The change in strain of the Bragg grating causes a change in an optical response of the Bragg grating to light that is in use guided to the Bragg grating so that the change in strain and hence the local change in longitudinal external movement can be detected with the apparatus in accordance with the present invention.

In one embodiment at least a portion of the Bragg grating is positioned between the holder and the contact region. The apparatus typically is arranged so that a motion of the further region in a direction along the length of the optical fibre causes a force in a longitudinal direction on the Bragg grating.

The holder typically comprises a rigid support that is rigidly attached to the length of the optical fibre at an attachment region in a manner such that at least a portion of the Bragg grating is positioned between the attachment region and a contact region. The contact region typically is a region of a movable member to which the length of the optical fibre is attached. The movable member may be provided in the form of a slider that is arranged to slide on a portion of the rigid support.

In one embodiment of the apparatus the Bragg grating is one of a plurality of Bragg gratings positioned in the length of the optical fibre. The apparatus comprises in this embodiment a first and a second the Bragg grating. The support is in this case arranged for attachment to the length of the optical fibre at least two attachment regions between which the first and second two Bragg gratings are positioned. The movable member may be rigidly coupled to the length of the optical fibre at a position between the first and the second Bragg gratings whereby the apparatus is arranged so that movement of the contact region in a first direction along the length of the optical fibre causes an increase in strain of one of the first and second Bragg gratings and a decrease in strain of the other one of the first and second Bragg gratings.

The element for reducing an impact of an external transversal force typically is rigid and protects each or a respective Bragg grating.

In one embodiment the apparatus comprises a catheter in which the length of the optical fibre, the movable member and the support are positioned. In this case and the contact region is in direct or indirect contact with an interior surface of the catheter so that movement of an external surface, when in contact with an external surface of the catheter at the contact region, causes movement of the movable element and a change in strain of the at least one Bragg grating.

The apparatus for sensing a motion may be used in any environment, including in particular an in-vivo-environment. The apparatus for sensing a motion typically comprises a bio-compatible exterior surface material.

In an alternative embodiment at least a portion of the Bragg grating is positioned between two holders to which the portion of the Bragg grating is rigidly attached. In this embodiment the apparatus typically is arranged so that a motion of the further region along the length of the optical fibre portion causes a force in a transversal direction on the Bragg grating. The apparatus comprises in this case typically a movable member. The contact region typically is an exterior region of the movable member and the apparatus typically is arranged so that movement of the movable member along the length of the optical fibre causes the force in the transversal direction.

The present invention provides in a second aspect a series of apparatus comprising a plurality of the above-defined apparatus.

The lengths of the optical fibres of the apparatus may be spliced together.

The length of the optical fibre of the series of apparatus may be a first length of optical fibre and the series of apparatus may further comprise a second length of optical fibre. The first length of optical fibre may cross over a portion of the second length of optical fibre between adjacent apparatus of the series of apparatus. Portions of the second length of optical fibre may also be positioned parallel to the Bragg gratings of the first optical fibre portion.

In one embodiment each apparatus comprises a rigid support that is coupled to a respective portion of the first length of optical fibre at attachment regions. In this embodiment the portions of the second length of the optical fibre are also attached to the support at attachment regions that are aligned with the attachment regions of the portions of the first length of optical fibre.

The series of apparatus may comprise at least one apparatus for pressure sensing which comprises:
  an optical fibre portion comprising a Bragg grating; and
  a moveable wall portion having opposite first and second sides, the moveable wall portion being positioned so that a change in pressure at one of the sides relative to a pressure at the other side will move the moveable wall portion, the moveable wall portion being coupled to the Bragg grating so that the movement of the moveable wall portion causes a force on the Bragg grating, the force having a component that is transversal to the Bragg grating and being applied from one side of the Bragg grating whereby a change in tensile strain of the Bragg grating is effected.

The present invention provides in a third aspect an apparatus for sensing a motion, the apparatus comprising:
  an elongated element having an interior region and at least a portion of the elongated member being flexible, the or each portion of the elongated element being more compressible or extendable in the direction of elongation than in a transversal direction; and
  an optical fibre comprising at least one Bragg grating, at least a portion of the optical fibre being located within the interior region of the elongated element and being attached to the elongated element;
  wherein the apparatus is arranged so that the flexibility of the or each portion of the elongated element enables a longitudinal movement of a first portion of the elongated element relative to a second portion of the elongated element and wherein the Bragg grating is positioned so that the movement of the first portion causes a change in strain of the Bragg grating.

The elongated element may be a member that is formed at a position remote from the optical fibre portion and to which the optical fibre portion is then attached.

The elongated element typically is arranged so that the optical fibre portion is largely protected from compression in a transversal direction.

The elongated element may be a tube in which the optical fibre portion is positioned. Alternatively, the elongated element may comprise a spiral. In one specific embodiment the elongated element is provided in the form a coil spring.

The elongated element may be composed of any suitable material, including polymeric materials and metallic materials. Further, the elongated element may be provided in the form of a coating.

The optical fibre portion may be elastically attached to the elongated element. For example, the optical fibre portion may be elastically attached to the elongated element along the majority of the length portion of the optical fibre portion that is positioned within the interior region of the elongated element. In one specific embodiment the optical fibre portion is elastically attached to the elongated element along substantially the entire length of the optical fibre portion that is positioned within the interior region of the elongated element.

Alternatively, the optical fibre portion may be rigidly attached at attachment regions that are spaced apart along a portion of the length of the elongated element.

The optical fibre portion may be attached to the elongated element using an adhesive material. In one embodiment the optical fibre portion is attached to the elongated element by applying the adhesive material at one or more regions of the optical fibre portion that is positioned within the elongated element.

In one specific example the elongated element is a coil spring and the coil spring with the optical fibre portion, positioned within the interior region of the coil spring, may be dipped into the adhesive material to cause adhesion.

In an alternative variation the elongated element is formed at the optical fibre portion and may for example be provided in the form of a coating.

The apparatus for sensing a motion may also comprise a plurality of optical fibre portions that are positioned within the interior region of the elongated element. Each optical fibre portion may comprise a Bragg grating and at least two of the Bragg gratings may be positioned at different positions along the length of the elongated element so that sensing of a distribution of the longitudinal motion is possible.

Further, the elongated element may comprise transversal external projections that are arranged to facilitate frictional engagement with an external medium, such as the oesophageus, with the apparatus. For example, the projections may be provided in the form of regions of increased diameter of the elongate element.

In addition, the or each portion of the elongated element typically is also more flexible in the direction of elongation than in a transversal direction.

The present invention provides in a fourth aspect a method of sensing a motion in an in-vivo environment, the method comprising:
  inserting an optical fibre portion, or an assembly including the optical fibre portion, into a body lumen so that side-portions of the optical fibre portion, or the assembly including the optical fibre portion, are in frictional contact with walls of the body lumen, the optical fibre portion comprising at least one Bragg grating;
  exposing the optical fibre portion, or the assembly including the optical fibre portion, to a motion of the body lumen in a direction along the optical fibre portion in a manner such that the Bragg grating experiences a change in strain; and
  detecting an optical response from the Bragg grating that is indicative of the change in strain.

The invention will be more fully understood from the following description of specific embodiments of the invention. The description is provided with reference to the accompanying drawings.

BRIEF DESCRIPTION OF THE DRAWINGS

FIGS. 2 (*a*) and (*b*) show side and end views, respectively, of an apparatus for sensing a motion according to a specific embodiment of the present invention;

DETAILED DESCRIPTION OF SPECIFIC EMBODIMENTS

Figure 1:
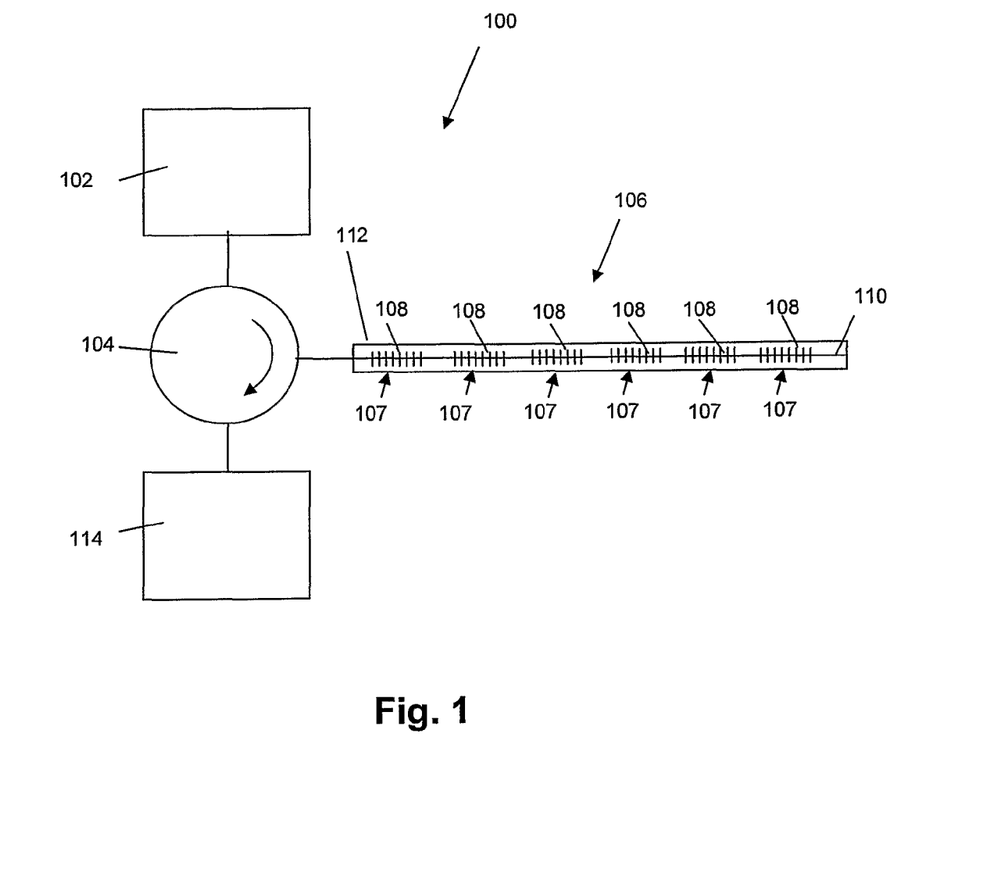
FIG. 1 shows a system for sensing a motion according to a specific embodiment of the present invention.

Referring initially to FIG. 1, a system for sensing a motion according to a specific embodiment of the present invention is now described. The system 100 comprises a light source 102 which in this embodiment is a broadband light source commonly referred to as a "white" light source even though the light that is emitted by the light source 102 may have any wavelength range.

The light is directed via optical circulator 104 to a series of apparatus for sensing a motion 106. In a variation of this embodiment the optical circulator 104 may be replaced by an optical coupler, an optical splitter or an optical beam splitter.

Each apparatus 107 of the series 106 comprises a Bragg grating 108 which are formed in an optical fibre portion 110. Side-portions of the apparatus 107 frictionally engage with a medium, such as the oesophagus, that in use surrounds the apparatus 107. A local change in force or strain, associated with a longitudinal motion, may be applied from the oesophagus to a first portion of the series 106. The series 106 is arranged so that the external motion in a longitudinal direction effects a longitudinal movement of a first portion of a one or more apparatus 107 relative to a second portion of the or a respective apparatus 107. The relative movement causes a change in strain of the or a respective Bragg grating 108 and the change in strain causes a change in an optical property of the or a respective Bragg grating 108, such as a change in an optical path length, which influences an optical response of the or a respective Bragg grating 108 to guided light. Consequently it is possible to detect a change in the longitudinal external motion by analysing the optical response from the Bragg gratings 108.

In this embodiment each Bragg grating 108 of the series has a slightly different refractive index variation so that each Bragg grating 108 has a slightly different spectral response. The light that is produced by the light source 102 and that is directed to the Bragg gratings 108 therefore causes unique responses from the Bragg gratings 108 and which are directed via the optical circulator 104 to optical analyser 114 for optical analysis. Such a procedure is commonly referred to as wavelength division multiplexing (WDM). The Bragg gratings may also cause optical responses which overlap in wavelength or frequency space as long as sufficient information is known about each Bragg grating to allow the signals to be successfully deconvolved.

In a variation of this embodiment at least some of the Bragg gratings 108 may be identical and consequently, if the strain conditions are the same, their optical response will also be the same. In this case a pulsed light source may be used to guide light to the Bragg gratings 108 and the positions of the Bragg gratings 108 may be estimated from a time at which the responses are received by the optical analyser 114.

Optical frequency domain reflectometry (OFDR) techniques may also be used to identify a change in an optical response of a particular Bragg grating 108. In this case a tunable laser is used to provide light having a frequency that is swept constantly. A portion of the laser light is reflected by a reflector to provide a reference signal. A response signal from each one of the Bragg gratings 108 will interfere with the reference signal, but due to the sweeping frequency of the laser and the differing positions of the Bragg gratings 108, the response from each Bragg grating 108 will result in a unique beat frequency on the detected signal. Fourier transformation techniques are then used to identify the response of a particular Bragg grating 108 amongst other ones of the Bragg gratings 108.

It will be appreciated that in a further variation the apparatus may be arranged so that responses from respective Bragg gratings can be analysed by receiving light that is transmitted through the Bragg gratings 108. For example, in this case the apparatus 106 typically is arranged so that light is guided from the light source 102 through the Bragg gratings 108 and then directly to the optical analyser 114.

Each Bragg grating 108 is written into an optical fibre and spliced between fibre portions. In alternative embodiments the Bragg gratings 108 may be written into one optical fibre and the optical fibre portion may be integrally formed.

In variations of this embodiment the apparatus may also comprise a plurality of Bragg gratings associated with respective optical fibre portions that are arranged in parallel.

Figure 2:
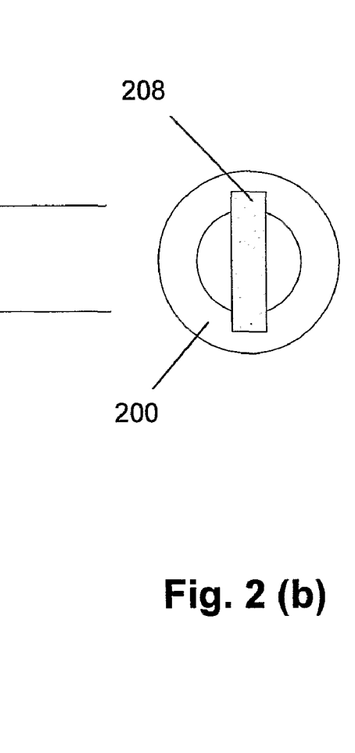

FIG. 2 shows an apparatus 107 for pressure sensing in further detail. The apparatus comprises a portion of the optical fibre 110 and a Bragg grating 108. The portion of the optical fibre 110 is attached to a support 200 at attachment regions 202 and 204. The support 200 is a rigid structure that is this embodiment formed from stainless steel or another suitable material. The portion of the optical fibre 110 is rigidly attached at attachment regions 202 and 204 using a suitable adhesive. The support 200 comprises a cylindrically shaped inner portion and cylindrically shaped end portions that have a diameter larger than the inner portions.

The apparatus 107 also comprises a sliding member 206 (in the following referred to as "slider") that is substantially ring shaped and has an inner diameter that is larger than the diameter of the inner portion of the support 200 so that the slider 206 can slide on the inner portion of the support 200.

The portion of the optical fibre 110 is rigidly attached at the slider 206 at attachment region 208 using a suitable adhesive. Further, the portion of the optical fibre comprises in this embodiment an additional Bragg grating 210. The apparatus 107 is arranged so that the Bragg gratings 108 and 210 are positioned between attachment regions 202 and 204 and the attachment region 208 is located between the Bragg grating 108 and 210.

At least a portion of the apparatus 107 may be surrounded by a protective diaphragm that is formed from a suitable elastic polymeric material (the diaphragm is not shown).

The series 106 of apparatus 107 is typically positioned in a catheter that is arranged for positioning in an interior portion of a body lumen such as the oesophagus. The series 106 comprises an anchoring element (not shown) that anchors an end portion of the series 106 at a body opening, such as a surface of the nose of the patient.

In this embodiment the apparatus 107 is arranged so that an outer surface of the slider 206 frictionally engages with the diaphragm, which in turn frictionally engages with an inner portion of the catheter. A longitudinal movement of bolus in the oesophagus or a longitudinal movement of inner wall portions of the oesophagus, when in contact with an exterior portion of the catheter, moves the slider 206 relative to the support 200 and the movement of the slider 206 causes a change in strain of the Bragg gratings 210, which is indicative of the longitudinal movement and can be analysed using the above described procedures.

If the apparatus 107 is exposed to a uniform change in temperature, the Bragg gratings 108 and 210 will experience the same uniform extension or contraction in response to the change in temperature. However, the movement of the slider 206 relative to the support 200 in response to an external longitudinal motion causes the strain in one of the gratings to increase and the other one to decrease. Consequently, by analysing the responses from both Bragg gratings it is possible to analyse which portion of a detected change in strain is caused by a change in temperature and an output of the apparatus 107 can be compensated for an influence of a uniform chance in temperature.

The apparatus 107 also comprises protective rigid projections that surround the Bragg gratings 108 and 210 so that the Bragg gratings 108 and 210 are protected from transversal forces in the body lumen.

The series 106 of apparatus 107 is typically anchored at an external portion of the body of the patient, such as the nose. Further, the oesophagus typically exerts transversal forces onto the series 106 of apparatus 107 when positioned in the oesophagus whereby the series 106 of apparatus 107 is locally and temporarily held in position.

The apparatus 107 comprises in this embodiment an additional optical fibre portion 214 that is positioned parallel the optical fibre portion 110. The optical fibre portion 214 is rigidly attached at attachment regions 216 and 218 to support 200 using a suitable adhesive. The optical fibre portion 214 is in this embodiment used to guide optical signal associated with further detection devices. For example, as will be discussed below, the series 106 of apparatus 107 may also comprise at least one apparatus for measuring a pressure in the body lumen.

In a variation of the described embodiment the Bragg grating the optical fibre 214 may also comprise a series of Bragg gratings that may be used for providing accurate information about an effect of a change in temperature on the output of the series of apparatus 106.

Figure 3:
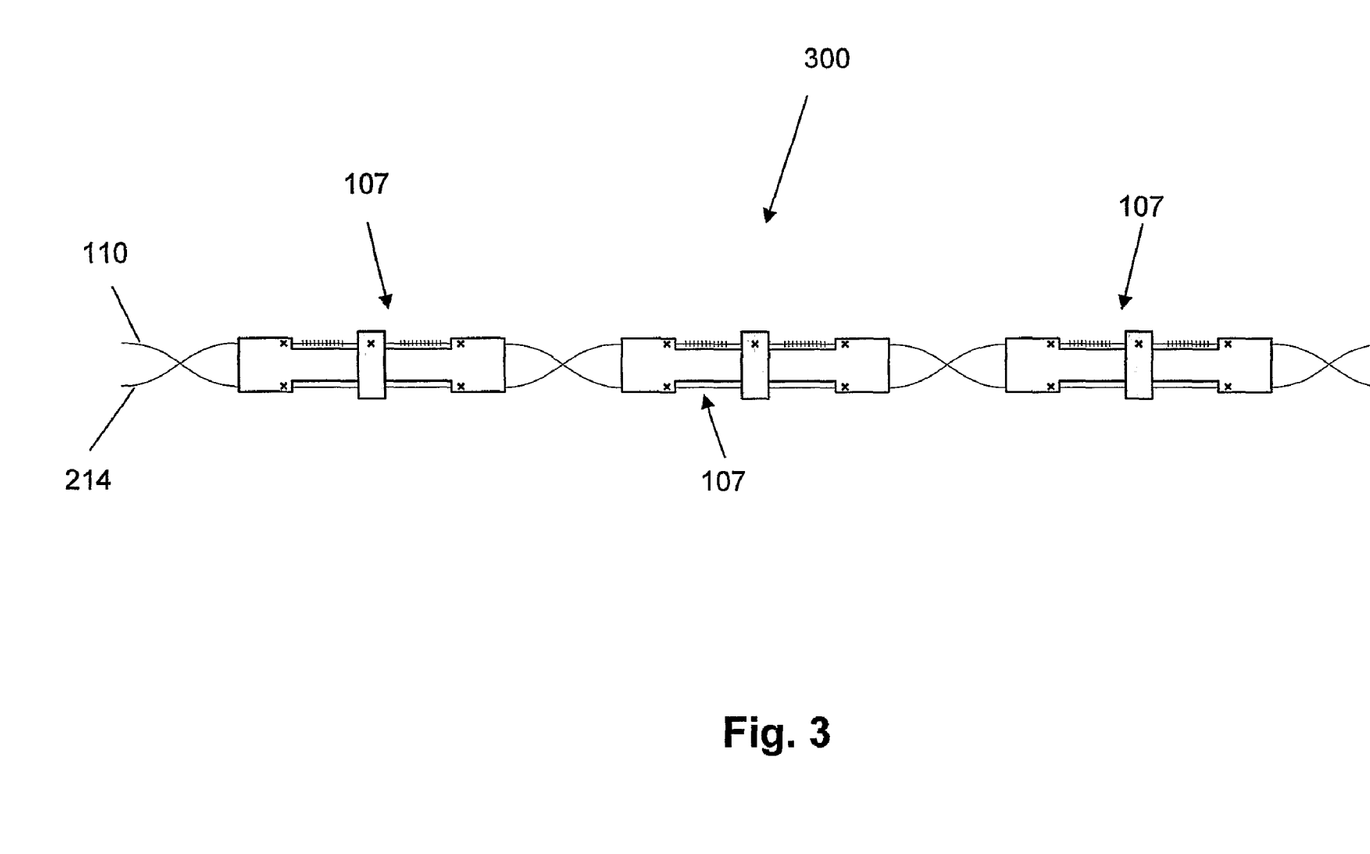
FIG. 3 shows a series of apparatus for sensing a motion according to a specific embodiment of the present invention.

FIG. 3 shows a series 300 of 3 apparatus 107. In this embodiment the optical fibers 110 and 214 cross each other between adjacent apparatus 107. Consequently, both optical fibers carry in this embodiment information associated with detection of the longitudinal motion. The crossing of the optical fibre portions 110 and 214 between adjacent apparatus 107 results in increased mechanical flexibility of the series 106.

Figure 4:
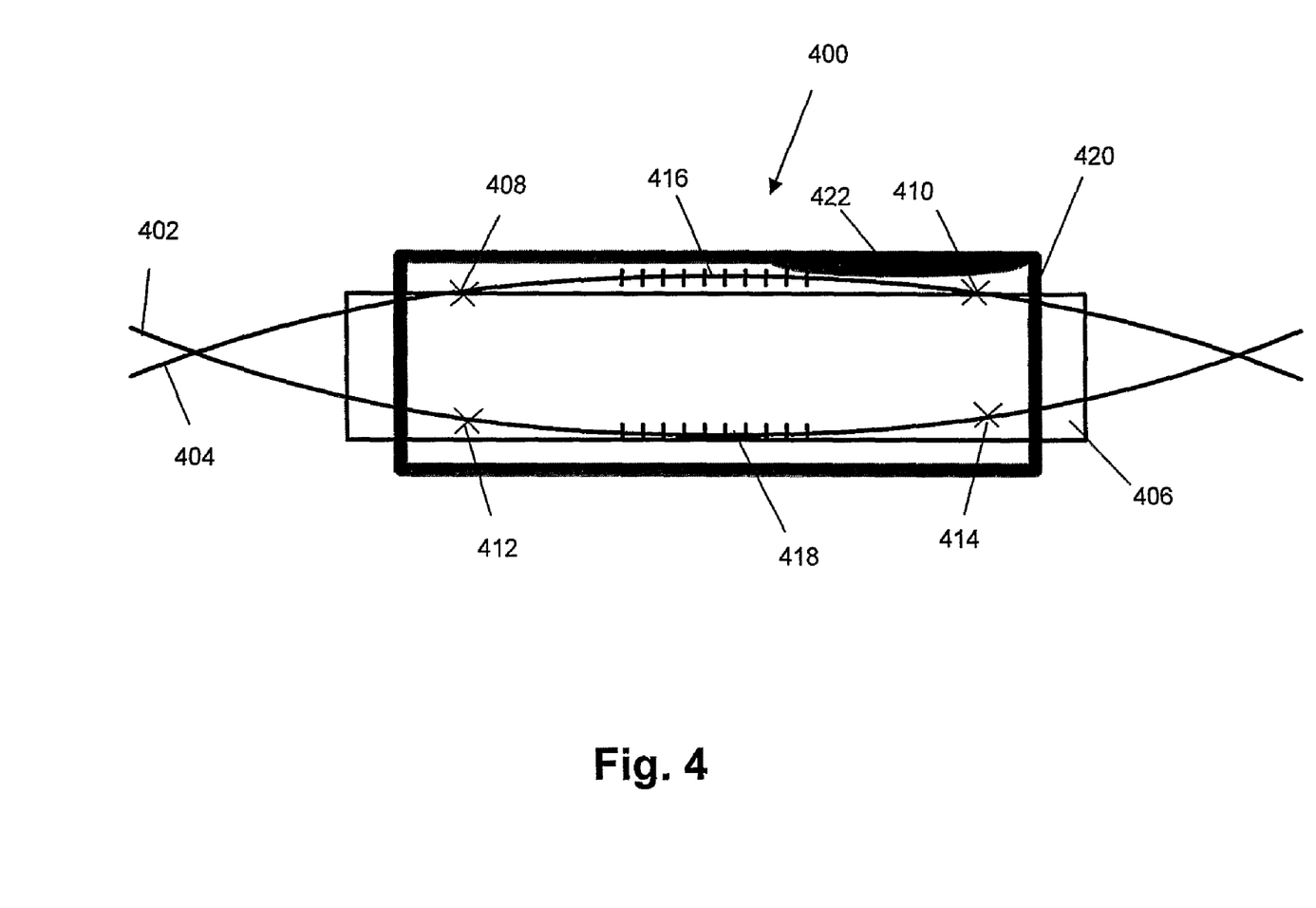
FIG. 4 shows an apparatus for sensing a motion according to a specific embodiment of the present invention.

FIG. 4 shows an apparatus 400 for sensing a motion in accordance with a further specific embodiment of the present invention. The apparatus 400 may replace any one of the apparatus 107 of the series of apparatus 106 shown in FIG. 1. In this embodiment the apparatus 400 comprises optical fibre portions 402 and 404. The optical fibre portions 402 and 404 are attached to a rigid support 406 at attachment regions 408, 410, 412 and 414. The optical fibre portions 404 and 402 comprise Bragg gratings 416 and 418 that are positioned between attachment regions.

The apparatus 400 also comprises a sliding member 420 that is arranged for sliding along the support 406. The sliding member 420 has a hollow cylindrical shape and comprises an inter projection 422. The apparatus 400 is in this embodiment arranged so that a longitudinal motion of the sliding member 420 along the structure 406 in a direction towards the left hand of the representation shown in FIG. 4 moves a region of the optical fibre portion 404 and imparts a transversal force on the Bragg grating 416.

Consequently, if an exterior surface, such as a surface of the oesophagus, is frictionally engaged with an outer surface of the sliding member 420, a suitable movement of the oesophagus effects a movement of the sliding member 420 and a transversal force on the Bragg grating 416 and the Bragg grating 416 will experience a change in strain which is detectable in the above described manner.

The Bragg grating 418 is in this embodiment provided in order to enable compensation for an effect of temperature changes. As the Bragg grating 418 is not exposed to a force that results from the motion of the sliding member 420, the Bragg grating 418 will only experience a change in strain if the temperature changes. If both gratings 418 and 416 experience the same change in temperature, it is possible to compensate an output associated with a strain change of the Bragg grating 416 for an influence of the temperature change.

It is to be appreciated that further variations and technical implementations of the apparatus 400 are possible. For example, the apparatus 400 may comprise a suitable lever arrangement or an arrangement that comprises wedge portions that are arranged to transform a force in a longitudinal direction into a force that acts on the Bragg grating 416 in a transversal direction.

Figure 5:
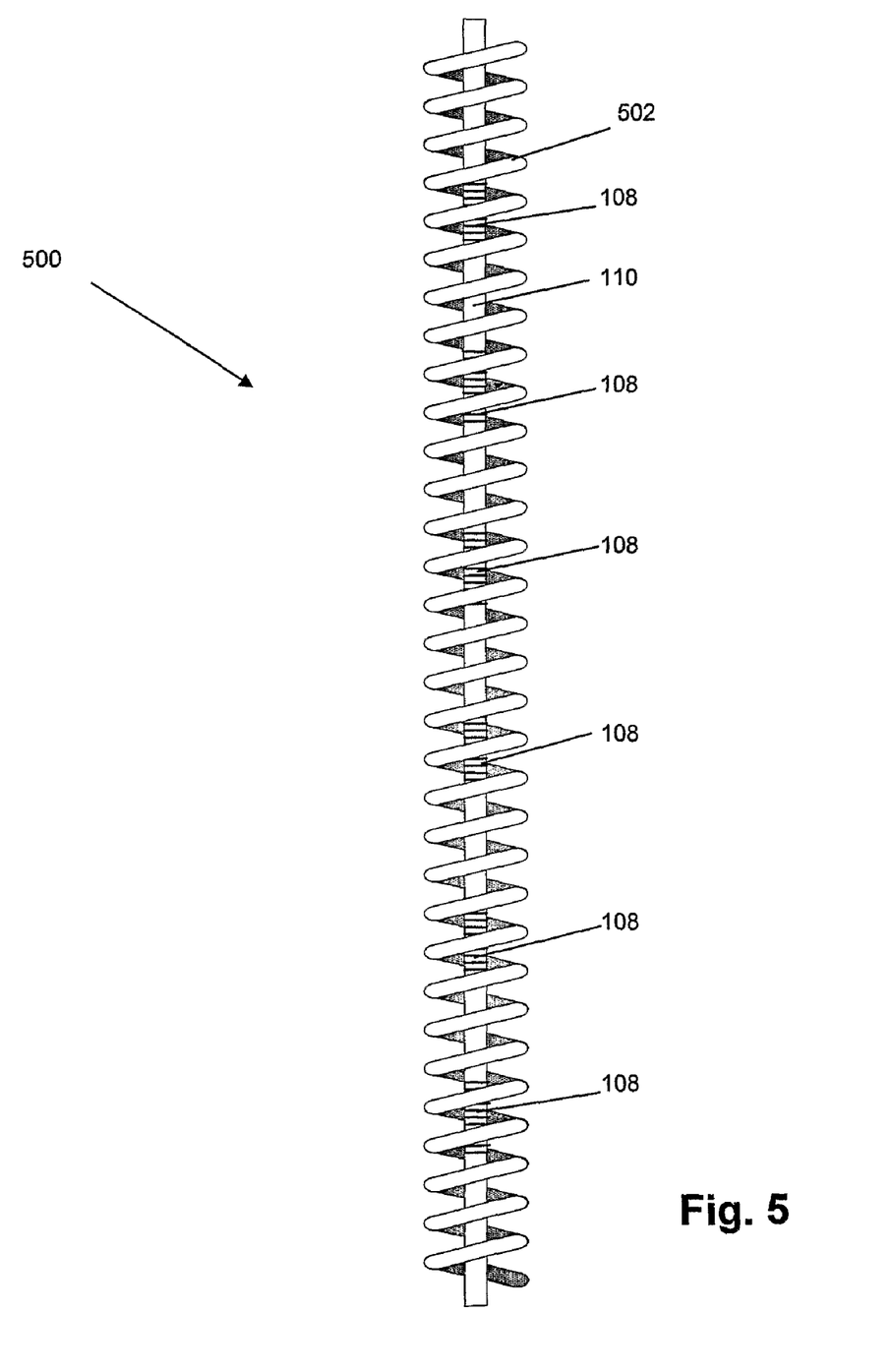
FIG. 5 shows an apparatus for sensing a motion according to another specific embodiment of the present invention.

FIG. 5 shows schematically an apparatus for sensing a motion in accordance with another specific embodiment. The apparatus 500 comprises a coil spring 502 in which the optical fibre portion 110 with the Bragg gratings 108 is positioned. The optical fibre portion 110 is in this example attached to the coil spring 502 along the entire length of the optical fibre portion 110.

In this embodiment, the apparatus 500 was assembled by positioning the optical fibre portion 110 in the interior of the coil spring 502 and then dipping the coil spring 502 with the optical fibre portion 110 in a suitable liquid adhering material that is bio-compatible when cured and forms an elastic mass that elastically attaches the optical fibre portion 110 to the coils spring 502 and also provides a bio-compatible exterior surface.

In this embodiment the optical fibre portion is elastically attached to the elongated element. In a variation of the embodiment, the optical fibre portion may be rigidly attached at attachment regions, which are spaced apart along a portion of the length of the coil spring 502.

Side-portions of the apparatus 500 frictionally engage with a medium, such as the oesophagus, that in use surrounds the apparatus 500. A local change in force or strain, associated with a longitudinal motion, may be applied from the oesophagus to a first portion of the apparatus 500. The apparatus 500 is arranged so that the external motion in a longitudinal direction effects a longitudinal movement of a first portion of the coil spring 512 relative to a second portion that may remain localised if the external medium does not move at the second portion. The relative movement causes a change in strain of one of Bragg gratings 108 and the change in strain causes a change in an optical property of the Bragg grating 108, such as a change in an optical path length, which influences an optical response of the Bragg grating 108 to light guided to the Bragg grating 108.

The apparatus 500 was assembled so that the Bragg gratings 108 experience a slight tensile strain when no external longitudinal force/strain is applied.

Figure 6:
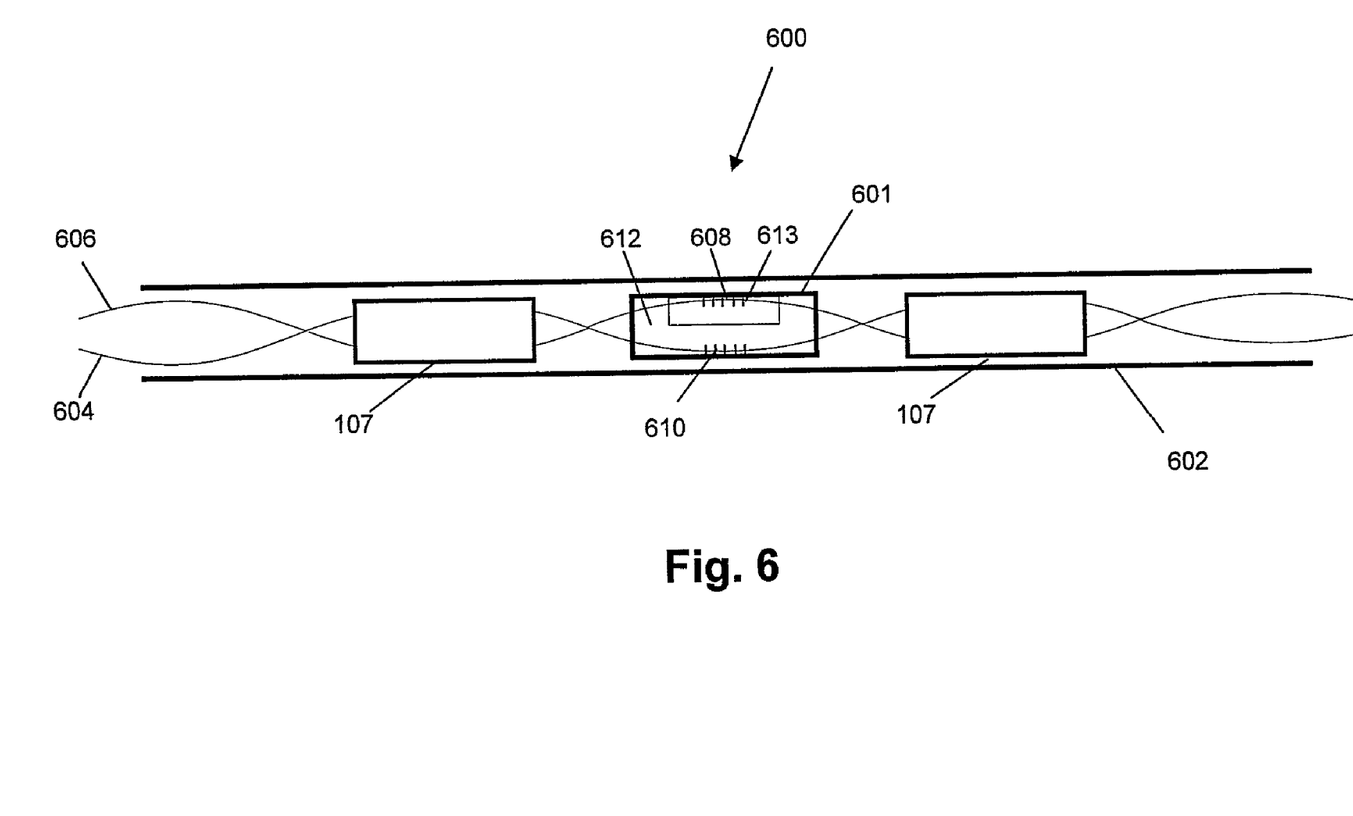
FIG. 6 shows an apparatus for sensing a motion according to a further specific embodiment of the present invention.

FIG. 6 shows an apparatus for sensing a motion in accordance with a further embodiment of the present invention. The apparatus 600 comprises the previously described apparatus 107 and an apparatus 601 for pressure sensing that form a series of apparatus. The series of apparatus is positioned in a catheter 602 and comprises optical fibres 604 and 606.

In this embodiment the apparatus 601 comprises Bragg gratings 608 and 610 which are formed in the optical fibres. The apparatus 601 comprises a rigid member 612 that has a movable wall portion which is provided in the form of a diaphragm 613. In this embodiment, portions of the optical fibre 604 and 606 are rigidly connected at attachment regions of the rigid member 612 so that the each Bragg grating 608 and 510 are positioned between two immediately adjacent attachment regions.

The Bragg grating 608 is positioned at a window of the rigid member 612 and on or near the diaphragm 613 such that an external pressure change effects movement of the diaphragm which in turn causes a change in strain of the Bragg grating 608. The change in strain causes a change of an optical property of the Bragg grating 608 such as a change of an optical path length, which influences optical responses of the Bragg grating 608.

The Bragg grating 610 is positioned so that a change in external pressure will not cause a change in strain of the Bragg grating 610 and this Bragg grating is provided in order to detect local changes in strain that are a result of local changes in temperature. For example, detected changes in strain of the Bragg grating 610 may be subtracted from detected changes in strain of the Bragg grating 608 to correct the responses from the Bragg grating 608 for temperature related changes.

Further details regarding an apparatus for pressure sensing are disclosed in PCT international application PCT/AU2006/000310 which is hereby incorporated by cross reference.

It is to be appreciated that the present invention may be provided in many different forms. For example, the apparatus 107 may comprise any number of optical fibre portions and any number of Bragg gratings. In addition, it is to be appreciated that the apparatus 107 may be provided in different shapes and different technical implementations. Further, the apparatus 500 may not comprise a coil spring and the elongated element may be provided in the form of a tube or another suitable form. The apparatus 500 may also comprise only one Bragg grating. In addition, the apparatus 500 may comprise a plurality of Bragg gratings which are located within a plurality of parallel optical fibre portions that are positioned within the elongated element. Each optical fibre portion may be individually coupled to the optical circulator 114 or the optical fibre portions may be coupled to each other using suitable optical couplers. Further, the apparatus 600 may comprise more than one apparatus for pressure sensing so that a distribution of pressures is detectable.

The reference that is being made to PCT international application PCT/AU2006/000310 does not constitute an admission that this PCT international application is part of the common general knowledge in Australia or any other country

The invention claimed is:

1. An apparatus for sensing a motion, the apparatus comprising:
   a length of an optical fibre comprising a Bragg grating;
   an element for reducing an impact of an external force that is transversal to the Bragg grating;
   a contact region coupled to a first portion of the length of the optical fibre and arranged so that movement of a further region, that is in direct or indirect contact with the contact region and moves relative to the apparatus in a direction along a portion of the apparatus, causes movement of the length of the optical fibre at the first optical fibre portion; and
   a holder arranged for reducing movement of the length of the optical fibre at a second portion of the length of the optical fibre when the optical fibre portion is moved at the first optical fibre portion;
   wherein the apparatus is arranged so that movement of the contact region relative to the holder causes a change in strain of the Bragg grating.

2. The apparatus of claim 1 wherein at least a portion of the Bragg grating is positioned between the holder and the contact region.

3. The apparatus of claim 1 wherein the apparatus is arranged so that a motion of the further region in a direction along the length of the optical fibre causes a force in a longitudinal direction on the Bragg grating.

4. The apparatus of claim 1 wherein the holder comprises a rigid support that is rigidly attached to the first portion of the optical fibre at an attachment region.

5. The apparatus of claim 4 wherein the contact region is a region of a movable member.

6. The apparatus of claim 5 wherein the movable member is provided in the form of a slider that is arranged to slide on a portion of the rigid support.

7. The apparatus claim 5 wherein the Bragg grating is one of at least two Bragg gratings positioned in the length of the optical fibre and wherein the support is arranged for attachment to the length of the optical fibre portion at least two attachment regions between which the at least two Bragg gratings are positioned and wherein the movable member is rigidly attached to the length of the optical fibre portion at a position between a first and a second Bragg gratings whereby the apparatus is arranged so that movement of the contact region in a first direction along the length of the optical fibre causes an increase in strain of one of the first and second Bragg gratings and a decrease in strain of the other one of the first and second Bragg gratings.

8. The apparatus of claim 5 comprising a catheter in which the length of the optical fibre, the movable member and the support are positioned and wherein the contact region is in direct or indirect contact with an interior surface of the catheter so that movement of an external surface, when in contact with an external surface of the catheter at the contact region, causes movement of the movable element and a change in strain of the at least one Bragg grating.

9. The apparatus of claim 4 wherein the Bragg grating is one of at least two Bragg gratings positioned in the length of the optical fibre and wherein the support is arranged for attachment to the length of the optical fibre portion at least two attachment regions between which the at least two Bragg gratings are positioned.

10. The apparatus of claim 1 wherein the element for reducing an impact of an external transversal force is rigid and protects each or a respective Bragg grating from such a force.

11. A series of apparatus comprising a plurality of the apparatus as claimed in claim 1.

12. The series of apparatus of claim 11 wherein the lengths of optical fibres are spliced together.

13. The series of apparatus of claim 11 wherein the length of the optical fibre of the series of apparatus is a first length of optical fibre and the series of apparatus further comprises a second length of optical fibre and wherein the first length of optical fibre crosses over a portion of the second length of the optical fibre between adjacent apparatus of the series of apparatus.

14. The series of apparatus of claim 11 comprising first and second optical fibres and wherein portions of the second optical fibres are positioned parallel to the Bragg gratings of the first optical fibre portion.

15. The series of apparatus of claim 14 wherein each apparatus comprises a rigid support that is coupled to a respective portion of the first length of the optical fibre at attachment regions and wherein the portions of the second length of optical fibre are attached to the support at attachment regions that are aligned with the attachment regions of the portions of the first length of optical fibre.

16. The series of apparatus of claim 11 comprising at least one apparatus for pressure sensing which comprises:
   an optical fibre portion comprising a Bragg grating; and
   a moveable wall portion having opposite first and second sides, the moveable wall portion being positioned so that a change in pressure at one of the sides relative to a pressure at the other side will move the moveable wall portion, the moveable wall portion being coupled to the Bragg grating so that the movement of the moveable wall portion causes a force on the Bragg grating, the force having a component that is transversal to the Bragg grating and being applied from one side of the Bragg grating whereby a change in tensile strain of the Bragg grating is effected.

17. The apparatus of claim 1 wherein at least a portion of the Bragg grating is positioned between two holders.

18. The apparatus of claim 1 wherein the apparatus is arranged so that a motion of the further region along the length of the optical fibre causes a force in a transversal direction on the Bragg grating.

19. The apparatus of claim 18 comprising a movable member, wherein the contact region is an exterior region of the movable member and wherein the apparatus is arranged so that movement of the movable member along the length of the optical fibre causes the force in the transversal direction.

* * * * *